United States Patent [19]

Kane et al.

[11] Patent Number: 4,946,856
[45] Date of Patent: Aug. 7, 1990

[54] 5-PHENYL-3H-1,2,4-TRIAZOL-3-ONES AND THEIR USE AS ANTICONVULSANTS

[75] Inventors: John M. Kane, Cincinnati; Francis P. Miller, Loveland, both of Ohio

[73] Assignee: Merrell Dow Pharmaceuticals Inc., Cincinnati, Ohio

[21] Appl. No.: 317,482

[22] Filed: Mar. 1, 1989

Related U.S. Application Data

[63] Continuation-in-part of Ser. No. 90,310, Aug. 27, 1987, abandoned, which is a continuation-in-part of Ser. No. 944,634, Dec. 19, 1986, abandoned.

[51] Int. Cl.$^5$ .............................................. A61K 31/41
[52] U.S. Cl. ................................... 514/384; 548/263.2
[58] Field of Search ......................... 514/384; 548/263

[56] References Cited

U.S. PATENT DOCUMENTS 3,514,466 5/1970 Stahle et al. .................... 514/384
4,414,221 11/1983 Parsons et al. ................... 514/384

FOREIGN PATENT DOCUMENTS

| 621842 | 2/1963 | Belgium | 548/263 |
|---|---|---|---|
| 894856 | 2/1983 | Belgium | 548/263 |
| 1126882 | 3/1960 | Fed. Rep. of Germany . | |
| 153953 | 2/1982 | German Democratic Rep. . | |
| 160447 | 3/1983 | German Democratic Rep. | 548/263 |
| 5063119 | 5/1975 | Japan | 548/263 |
| 6504121 | 4/1965 | Netherlands | 548/263 |
| 651537 | 3/1965 | South Africa | 548/263 |

OTHER PUBLICATIONS

G. Maffii, et al., Studio Faramacologico di Alcuni Ossadiazoli e Triazoli, *Farmaco* 13, 629–38 (1958). (Translation Provided).

M. Y. Mhassalkar, et al., Further Studies in Substituted 4H–1,2,4–Triazoles for Possible Hypoglycemic Activity, J. Med. Chem. 14, 1260–3 (1971).

F. P. Miller, et al., FASEB J. 2, A1070, Abstract 4501 (1988).

*Primary Examiner*—Glennon H. Hollrah
*Assistant Examiner*—Patricia L. Morris
*Attorney, Agent, or Firm*—Gary D. Street; Edlyn S. Simmons; Stephen L. Nesbitt

[57] ABSTRACT

This invention relates to 5-phenyl-3H-1,2,4-triazol-3-ones and to their use as anticonvulsants for treatment of seizure disorders.

9 Claims, No Drawings

5-PHENYL-3H-1,2,4-TRIAZOL-3-ONES AND THEIR USE AS ANTICONVULSANTS

This is a continuation-in-part of application serial number 90,310, filed Aug. 27, 1987, now abandoned, which is a continuation-in-part of application serial number 944,634, filed Dec. 19, 1986 now abandoned.

More specifically this invention relates to compounds of the formula

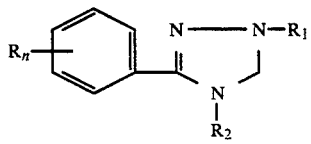

and the tautomers thereof, wherein
$R_1$ is hydrogen of $C_{1-4}$ lower alkyl,
$R_2$ is $C_{1-4}$ lower alkyl,
R is halogeno or trifluoromethyl, and n is zero, 1 or 2.

For R, preferably halogeno represents chloro or fluoro, with chloro being more preferred $R_1$ and $R_2$ are preferably methyl or ethyl, although any straight or branched $C_{1-4}$ lower alkyl group may be used. Compounds wherein $R_1$ is hydrogen are also preferred. The tautomeric forms are included for each of the compounds embraced within formula I wherein $R_1$ is H.

Preferably n is one, representing a mono-substituted phenyl moiety with the R-substitutent being located at the ortho, meta or para position, although the ortho- and para-substituted compounds are preferred. When the phenyl moiety is disubstituted (i.e., n is 2), substitution may be at the 2,3-; 2,4-; 2,5-; 2,6-; 3,4-; and 3,5- positions.

The use of triazol-3-ones of formula I as neuroprotectants for use in treatment of neurodegenerative disorders such as drug-induced parkinsonism, stroke, cerebral ischemia and Alzheimer's disease, is disclosed in copending application serial number 107,001, filed Oct. 16, 1987.

The pharmacological profile of these compounds and their relative potencies may readily be demonstrated through standard laboratory tests indicative of compounds known to be useful as anticonvulsants suitable for use in the treatment of seizure disorders. Compounds of formula I are particularly useful for treatment of idiopathic epilepsy, but their activity in a broad spectrum of laboratory tests is indicative of activity against most types of seizure disorders.

For example, in the evaluation and characterization of the anticonvulsant and GABAergic activity and to observe the pharmacological profile of the compounds of this invention, it is convenient to employ such tests as the antagonism of 3-mercaptopropionic acid-induced convulsions, an assay performed on mice wherein wild running fits or generalized seizures are induced by 3-mercaptopropionic acid; the antagonism of strychnine-induced seizures in mice; the antagonism to maximal electroshock, an assay performed in mice wherein seizures are caused by the administration of electroshock; and the antagonism to pentylenetetrazol, an assay to measure the prevention of seizures caused by administration of pentylenetetrazol.

Compounds that inhibit pentylenetetrazol-induced seizures in mice are known to possess anticonvulsant and antianxiety effects. An appropriate dose of test compound is administered to groups of mice and, at a selected time thereafter, pentylenetetrazol, prepared as a solution in distilled water such that 10 ml/kg delivers a dose of 60 mg/kg, is administered by rapid intravenous injection. Absence of clonic convulsions for 2 minutes after pentylenetetrazol is considered significant protection. Prevention of tonic extensor convulsions is also reported and usually occurs at a dose lower than that required to block clonic convulsions. Inhibition of clonic seizures induced by this dose of pentylenetetrazol is evidence of potential anticonvulsant/antianxiety activity. Against seizures caused by pentylenetetrazol, 5-(4-chlorophenyl)-2,4-dihydro-4-ethyl-2-methyl-3H-1,2,4-triazol-3-one has an $ED_{50}$ of 16.5 mg/kg.

Compounds that antagonize the tonic extensor seizures caused by strychnine have been shown to have muscle relaxant, spasmolytic, anticonvulsant and anxiolytic activities in man. The activity of the compounds can be demonstrated by the method of R. A. Turner, *Screening Methods in Pharmacology*, Chapter 14 (Academic Press, 1965). Groups of 10 to 20 male mice are administered one or more doses of test compound in an appropriate vehicle or, for comparison, the vehicle alone. At a selected time thereafter, strychnine sulfate, prepared as a solution in distilled water, is administered intraperitoneally at a dose of 2.7 mg/kg. Ninety-nine percent of vehicle-treated mice exhibit convulsions as this dose of strychnine. Absence of tonic extension for greater than 15 minutes after strychnine administration is considered significant protection. Treatment of mice with a dosage range of baclofen, a known antispastic-/muscle relaxant, of from 12.5 to 200 mg/kg i.p. causes over 50% antagonism of strychnine-induced seizures. In this assay, 5-(4-chlorophenyl)-2,4-dihydro-4-ethyl-2-methyl-3H-1,2,4-triazol-3-one has an $ED_{50}$ between 25 and 50 mg/kg.

In the test for antagonism to maximal electroshock, small groups of mice are administered one or more doses of test compound. At a selected time thereafter, an electroshock sufficient to cause tonic extension in 100% of contol mice is administered by means of corneal electrodes. The shock parameters are 50 mA, 120 V, 0.2 seconds. Inhibition of the tonic extensor component of the electroshock convulsion is indicative of anticonvulsant activity of the test material. Phenobarbital blocks in the dose range of 15-30 mg/kg, diphenylhydantoin in the range of 7.5-15 mg/kg. Both of these compounds are effective versus grand mal epilepsy. In this assay, 5-(4-chlorophenyl)-2,4-dihydro-4-ethyl-2-methyl-3H-1,2,4-triazol-3-one has an $ED_{50}$ between 25 and 50 mg/kg.

Antagonism of 3-mercaptopropionic acid-induced convulsions is measured by administering an appropriate dose of test compound to groups of mice and, at a selected time thereafter, administering 3-mercaptopropionic acid, prepared as a solution in distilled water (v/v, density =1.218 g/ml) such that 10 ml/kg contains the required dose, by rapid intravenous injection at a dose of 100 mg/kg. Mice are observed continuously for 5 minutes (mean latency of 100 controls =2.99 min ±0.94 S.D.) for development of seizures characterized by wild running fits, generalized clonic or clonic-tonic episodes. Absence of seizures for 5 minutes after administration of 3-mercaptopropionic acid is considered protection. In this assay, 5-(4-chlorophenyl)-2,4-dihydro-4-ethyl-2-methyl-3H-1,2,4-triazol-3-one has an $ED_{50}$ between 25 and 50 mg/kg.

The compounds of this invention will exert anticonvulsant activity useful in the treatment of idiopathic epilepsy and of other seizure disorders at oral dosage levels of about 0.25 to 25 mg/kg of body weight per day. Such doses are lower than the doses at which these compounds exhibit sedative action and are well below toxic doses of the compounds. Of course the degree of severity of the disease, the age of the patient and other factors normally considered by the attending diagnostician will influence the individual regimen for each patient. In general, the parenterally administered doses are about ¼ to ½ that of the orally administered dose.

For oral administration the compounds can be formulated into solid or liquid preparations such as capsules, pills, tablets, troches, powders, solutions, suspensions or emulsions. Solid unit dosage forms can be in the form of a capsule which can be of the ordinary gelatin type containing, for example, lubricants and inert fillers such as lactose, sucrose or cornstarch. In another embodiment the compounds of general formula I can be tableted with conventional tablet bases such as lactose, sucrose and cornstarch, in combination with binders such as acacia, cornstarch or gelatin, disintegrating agents such as potato starch or alginic acid, and a lubricant such as stearic acid or magnesium stearate.

For parenteral administration, the compounds may be administered as injectable dosages of a solution or suspension of the compound in a physiologically acceptable diluent with a pharmaceutical carrier which can be a sterile liquid such as water, alcohol, oils and other acceptable organic solvents, with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanol, glycols such as propylene glycol or polyethylene glycol, or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic ®, a silicone rubber manufactured by the Dow-Corning Corporation.

As is true for most classes of compounds generally suitable as therapeutic agents, certain subgeneric groups and specific members of that class, in the light of their overall biological profile, are preferred. In this instance the preferred R substituent is chloro, with chloro at the 2-or 4-positions of the aromatic ring being preferred. It is preferred that the $R_2$ alkyl substituent be methyl and ethyl, with hydrogen, methyl or ethyl being the preferred groups for $R_1$. Particularly preferred compounds are 5-(4-chlorophenyl)-2,4-dihydro-4-ethyl-2-methyl-3H-1,2,4-triazol-3-one 5-(4-chlorophenyl)-2,4-dihydro-2,4-diethyl-3H-1,2,4-triazol-3-one 5-(2-chlorophenyl)-2,4-dihydro-4-methyl-3H-1,2,4-triazol-3-one 5-(2-chlorophenyl)-2,4-dihydro-2,4-dimethyl-3H-1,2,4-triazol-3-one.

The compounds of Formula I may readily be prepared using processes and techniques analogously known in the art, for example in the method of S. Kuboda and M. Uda, *Chem. Pharm. Bull.* 21, 1342 (1979), as seen by the following reaction scheme:

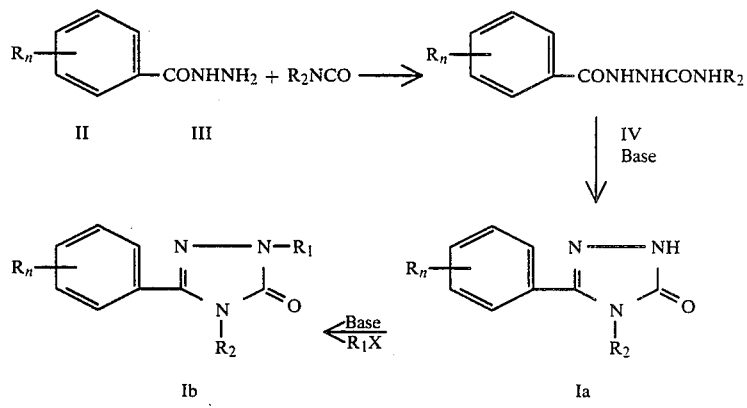

wherein R, n, $R_1$ and $R_2$ are as defined in formula I, and X is a suitable leaving group.

The preparation of the 1-benzoylsemicarbazides (IV) is readily effected by reacting a benzoyl hydrazide (II) with an $R_2$-substituted isocyanate (III) by contacting the reactants together in a suitable aprotic solvent, preferably one in which the hydrazide reactant is soluble, e.g., tetrahydrofuran (THF), $CHCl_3$, $CH_2Cl_2$, benzene, toluene, $Et_2O$ and the like. The reaction is quite rapid and may be carried out at from 0° C. to about room temperature and, although the reaction proceeds rapidly, the mixture may be left for 24 hours without any significant decrease in yield. The required hydrazides and isocyanates are readily available, but may be prepared by known techniques quite obvious to one of ordinary skill in the art.

The desired 5-phenyl-2,4-dihydro-4-alkyl-3H-1,2,4-triazol-3-ones (Ia) may be prepared by reacting the semicarbazides (IV) with a base, preferably an aqueous alkali metal hydroxide (e.g., NaOH, KOH) at about 50°-120° C., although reflux temperatures are preferred. Normal reaction time is about 7 hours, although 4–24 hours may be needed depending on the temperature of the mixture and the structure of the reactant.

The desired 2,4-disubstituted-2,4-dihydro-3H-1,2,4-triazol-3-ones (Ib) may be prepared by reacting the 4-substituted-2,4-dihydro-3H-1,24-triazol-3-ones (Ia)

with an appropriate $R_1X$ reactant wherein X is a suitable leaving group, e.g., Cl, Br, $OSO_2CF_3$ and the like. Preferably the reaction takes place in a solution of an aqueous alkali metal hydroxide, (e.g., KOH, NaOH) although more reactive bases (e.g., NaH, KH, LDA) may be used if the reaction is affected under aprotic dry conditions. The reaction preferably takes place at room temperatures over periods of about 18 hours to two weeks.

The following specific examples are given to illustrate the preparation of the compounds of this invention.

Preparation of Intermediate 1-Benzoyl-4-substituted semicarbazides

EXAMPLE 1

1-(4-Chlorobenzoyl)-4-ethylsemicarbazide

A stirred suspension of 4-chlorobenzoic acid, hydrazide (17.1 g, $1.00 \times 10^{-1}$ mole), and THF (425 ml) was warmed until homogeneous, at which time ethyl isocyanate (8.7 ml, $1.1 \times 0^{-1}$ mole) was added via syringe. A precipitate soon formed. After stirring overnight the reaction was diluted with $Et_2O$ and the precipitate was collected by filtration affording a colorless powder: 23.7 g (98%). Crystallization from ethanol gave a colorless solid: 21.4 g (88%), mp 237°–239°.

Preparation of 5-Phenyl-4-substituted-2,4-dihydro-3H-1,2,4-triazol-3-ones

EXAMPLE 2

5-(4-Chlorophenyl)-2,4-dihydro-4-ethyl-3H-1,2,4-triazol-3-one 1-(4-chlorobenzoyl)-4-ethylsemicarbazide (23.7 g, $9.81 \times 10^{-2}$ mole) and 1 molar aqueous NaOH (118 ml, $1.18 \times 10^{-1}$ mole) were stirred and warmed to reflux. After refluxing 23 hours, heating was discontinued and the reaction was acidified by the dropwise addition of 1 molar aqueous hydrochloric acid (130 ml, $1.30 \times 10^{-1}$ mole). A colorless solid formed as the reaction was acidified and, after cooling in an ice bath, this was collected by filtration. Crystallization from isopropanol gave colorless spars: 18.2 g (83%), mp 188°–189°.

Preparation of 5-Phenyl-2,4-dihydro-2,4-disubstituted-3H-1,2,4-triazol-3-ones

EXAMPLE 3

5-(4-Chlorophenyl)-2,4-dihydro-4-ethyl-2-methyl-3H-1,2,4-triazol-3-one

To a stirred, room temperature solution of 5-(4-chlorophenyl)-2,4-dihydro-4-ethyl-3H-1,2,4-triazol-3-one (6.00 g, $2.68 \times 10^{-2}$ mole) and 1 molar aqueous NaOH (30.0 ml, $3.00 \times 10^{-2}$ mole) was added a solution of methyl iodide (2.5 ml, $4.0 \times 10^{-2}$ mole) and ethanol (10 ml). After stirring overnight at room temperature, the reaction mixture was transferred to a separatory funnel where it was extracted three times with EtOAc. The EtOAc extracts were combined, washed with saturated aqueous NaCl, and dried over $Na_2SO_4$. The drying agent was removed by filtration and the filtrate was evaporated at reduced pressure leaving an oil which slowly solidified. Chromatography and crystallization from cyclohexane gave small colorless needles: 3.4 g (53%), mp 73°–75°.

In a similar manner the following compounds also may be prepared.

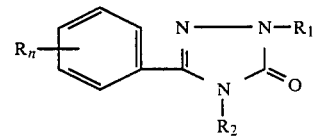

| $R_n-A_r$ | $R_1$ | $R_2$ | mp (°C.) |
| --- | --- | --- | --- |
| $C_6H_5$ | H | $CH_3$ | 177–178 |
| $C_6H_5$ | $CH_3$ | $CH_3$ | 140–141 |
| $C_6H_5$ | $C_2H_5$ | $CH_3$ | 87–89 |
| $C_6H_5$ | H | $C_2H_5$ | 163–165 |
| $2\text{-}ClC_6H_4$ | H | $CH_3$ | 168–170 |
| $2\text{-}ClC_6H_4$ | $CH_3$ | $CH_3$ | 61–63 |
| $4\text{-}ClC_6H_4$ | H | $CH_3$ | 213–215 |
| $4\text{-}ClC_6H_4$ | $CH_3$ | $CH_3$ | 126–128 |
| $4\text{-}ClC_6H_4$ | $C_2H_5$ | $CH_3$ | 79–81 |
| $4\text{-}ClC_6H_4$ | H | $C_2H_5$ | 188–189 |
| $4\text{-}ClC_6H_4$ | $CH_3$ | $C_2H_5$ | 73–75 |
| $4\text{-}ClC_6H_4$ | $C_2H_5$ | $C_2H_5$ | 62–64 |
| $4\text{-}ClC_6H_4$ | $n\text{-}C_3H_7$ | $C_2H_5$ | oil |
| $2\text{-}FC_6H_4$ | H | $CH_3$ | 189–191 |
| $2\text{-}FC_6H_4$ | $CH_3$ | $CH_3$ | 69–71 |
| $4\text{-}FC_6H_4$ | H | $CH_3$ | 216–218 |
| $4\text{-}FC_6H_4$ | $CH_3$ | $CH_3$ | 104–106 |
| $3,4\text{-}Cl_2C_6H_3$ | H | $CH_3$ | 170–172 |
| $3,4\text{-}Cl_2C_6H_3$ | $CH_3$ | $CH_3$ | 107–109 |

What is claimed is:

1. A method for the treatment of seizure disorders which comprises administering an anticonvulsant amount of a compound of the formula $R_1$ is hydrogen or $C_{1-4}$ lower alkyl, $R_2$ is $C_{1-4}$ lower alkyl, R is halogeno or trifluoromethyl, and n is zero, 1 or 2.

2. A method of claim 1 wherein $R_1$ is hydrogen, methyl or ethyl.

3. A method of claim 1 wherein $R_2$ is methyl or ethyl.

4. A method of claim 1 wherein n is 1 or 2 and R is halogeno.

5. A method of claim 4 wherein R is chloro.

6. A method of claim 5 wherein the compound is 5-(4-chlorophenyl)-2,4-dihydro-4-ethyl-2-methyl-3H-1,2,4-triazol-3-one.

7. A method of claim 5 wherein the compound is 5-(4-chlorophenyl)-2,4-dihydro-2,4-diethyl-3H-1,2,4-triazol-3-one.

8. A method of claim 5 wherein the compound is 5-(2-chlorophenyl)-2,4-dihydro-4-methyl-3H-1,2,4-triazol-3-one.

9. A method of claim 5 wherein the compound is 5-(2-chlorophenyl)-2,4-dihydro-2,4-dimethyl-3H-1,2,4-triazol-3-one.

* * * * *

UNITED STATES PATENT AND TRADEMARK OFFICE
CERTIFICATE OF CORRECTION

PATENT NO. : 4,946,856
DATED : August 7, 1990
INVENTOR(S) : Kane, et al

It is certified that error appears in the above-identified patent and that said Letters Patent is hereby corrected as shown below:

Column 1, Line 15 patent reads:

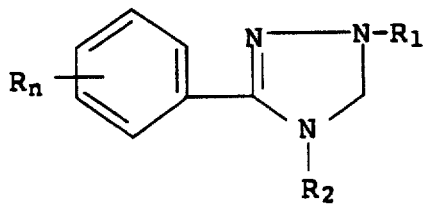

and should read:

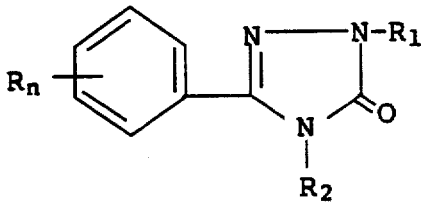

At Column 2, Line 37 patent reads: "eleotroshock" and should read: --electroshock--.

At Column 2, Line 41 patent reads: "contol" and should read: --control--.

UNITED STATES PATENT AND TRADEMARK OFFICE
CERTIFICATE OF CORRECTION

PATENT NO. : 4,946,856

DATED : August 7, 1990

INVENTOR(S) : Kane, et al

It is certified that error appears in the above-identified patent and that said Letters Patent is hereby corrected as shown below:

At Column 4, Line 68 patent reads "1,24-triazol" and should read: --1,2,4-triazol--.

At Column 5, Line 21 patent reads:
"(8.7 ml, 1.1 x $0^{-1}$ mole)" and should read:
--(8.7 ml, 1.1 x $10^{-1}$ mole)--.

Signed and Sealed this

Twenty-first Day of April, 1992

Attest:

HARRY F. MANBECK, JR.

*Attesting Officer*     *Commissioner of Patents and Trademarks*